United States Patent [19]

Umezawa et al.

[11] 4,430,346
[45] Feb. 7, 1984

[54] NOVEL CARCINOSTATIC SUBSTANCE AND PROCESS FOR SYNTHESIS THEREOF

[75] Inventors: Hamao Umezawa; Tomio Takeuchi, both of Tokyo; Shinichi Kondo, Yokohama; Hironobu Iinuma; Daishiro Ikeda, both of Tokyo; Teruya Nakamura, Kusatsu; Akio Fujii, Kamakura, all of Japan

[73] Assignee: Bristol-Myers Company, New York, N.Y.

[21] Appl. No.: 375,950

[22] Filed: May 7, 1982

[30] Foreign Application Priority Data

May 11, 1981 [JP] Japan .................................. 56-69340

[51] Int. Cl.³ ..................... C07C 129/12; A61K 37/02
[52] U.S. Cl. .................................... 424/311; 424/308; 424/312; 424/320; 560/251; 560/110; 564/159; 260/404.5
[58] Field of Search ................ 564/159; 424/320, 312, 424/311, , 308; 560/251, 110; 260/404.5

[56] References Cited

U.S. PATENT DOCUMENTS 3,436,463  4/1969  Mayhew et al. ..................... 564/159
4,041,077  8/1977  Ghosez et al. ....................... 564/159
4,334,097  6/1982  Schmidt ............................... 564/159

FOREIGN PATENT DOCUMENTS 2084999  4/1982  United Kingdom ............... 424/320

OTHER PUBLICATIONS

Shoji et al., J. Antibiotics, vol. 29, #4, pp. 390–393 (1976).
Umezawa et al., "Journal of Antibiotics", vol. 34, No. 12, pp. 1622–1624, 1981.
Kondo et al., "Journal of Antibiotics", vol. 34, No. 12, pp. 1625–1627, 1981.

Primary Examiner—James H. Reamer
Attorney, Agent, or Firm—Robert E. Carnahan

[57] ABSTRACT

The novel compound represented by the general formula (I)

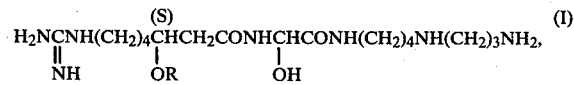

(wherein R represents a hydrogen atom, an alkanoyl group of 1 to 14 carbon atoms, or an arylcarbonyl group), and an acid addition salt thereof [on condition that when R is a hydrogen atom, the hydrochloride exhibits an optical rotation of $[\alpha]_D^{22} -1° \pm 2°$ (c, 2 water)] has antitumor activity in experimental animals.

15 Claims, No Drawings

NOVEL CARCINOSTATIC SUBSTANCE AND PROCESS FOR SYNTHESIS THEREOF

SUMMARY OF THE INVENTION

This invention relates to a new stereoisomeric form of the known antibiotic BMG162-aF2, namely, N-[4-(3-aminopropyl)aminobutyl]-2-[(S)-7-guanidino-3-hydroxyheptanamido]-2-hydroxyethanamide, the $C_{1-14}$ alkanoyl esters thereof at the 3-hydroxyl, the acid addition salts of each, and a process for their preparation. The following name is also appropriate (S)-7-[(aminoiminomethyl)amino]-N-[[2-[[4-[(3-aminopropyl)]amino]butyl]amino]-1-hydroxy-2-oxoethyl]-3-hydroxyheptanamide.

BACKGROUND OF THE INVENTION

The pending application of Umezawa et al. (Ser. No. 297,458 filed Aug. 28, 1981) refers to antibiotic substance BMG162-aF2 which is produced by the cultivation of a bacterium of the genus Bacillus. The present inventors have conducted an extensive study of antibiotic BMG162-aF2 and, as a result, have made the present invention.

DETAILED DESCRIPTION OF THE INVENTION

The novel compounds provided by the present invention are N-[4-(3-aminopropyl)aminobutyl]-2-[(S)-7-guanidino-3-hydroxyheptanamido]-2-hydroxyethanamide (referred to as GHA-GS) the hydrochloride salt of which exhibits the optical rotation $[\alpha]_D^{22} - 1° \pm 2°$ (c, 2 water) its 3-O-acyl derivatives N-[4-(3-aminopropyl)aminobutyl]-2-[(S)-7-guanidino-3-acyloxyheptanamido]-2-hydroxyethanamides represented by the general formula (I)

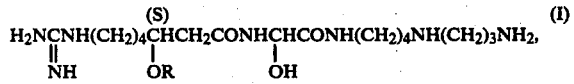

wherein R represents a hydrogen atom, an alkanoyl group of 1 to 14 carbon atoms, or an arylcarbonyl group such as benzoyl group, and acid addition salts thereof.

As examples of alkanoyl groups 1 to 14 carbon atoms represented by R of the general formula (I), mention may be made to acetyl group, propionyl group, butyryl group, pentanoyl group, hexanoyl group, heptanoyl group, octanoyl group, nonanoyl group, decanoyl group, undecanoyl group, lauroyl group, and tetradecanoyl group. These groups may be of branched chain. An example of arylcarbonyl groups represented by R is benzoyl group.

The physicochemical and biological properties of typical compounds of this invention are as shown below.

(I) Physicochemical Properties (1) GHA-GS hydrochloride is a colorless hygroscopic powder having no distinctly determinable melting point. It shows an optical rotation of $[\alpha]_D^{22} = -1° \pm 2°$ (c, 2 water). The elementary analysis coincides with the theoretical calculated for $C_{17}H_{37}N_7O_4 \cdot 3HCl$ (C 39.81%, H 7.86%, N 19.2%, Cl 20.73%). The proton NMR, as measured in heavy water, shows characteristic signals at $\delta = 1.8–2.3$ (CH$_2$ x 5), 2.57 (6''-CH$_2$), 2.95 (2-CH$_2$), 3.5–3.8 (NCH$_2$ x 5), 4.55 (3-CH) and 5.98 (2'-CH). Although the present compound and BMG162-aF2 are the same in two-dimensional structural formula, the present compound is different in optical rotation from BMG162-aF2 ($[\alpha]_D^{24} = -11° \pm 3°$). It is suggested, therefore, that the present compound is an epimeric mixture at position 2.

(2) The hydrochloride of 3-O-acetyl derivative of GHA-GS (briefly 3-O-acetyl-GHA-GS) is a colorless hygroscopic powder having no distinctly determinable melting point. It shows an optical rotation of $[\alpha]_D^{25} = +2° \pm 2°$ (c, 1 water). The elementary analysis coincides with the theoretical calculated for $C_{19}H_{39}N_7O_5 \cdot 3HCl \cdot 1.5H_2O$ (C 39.21%, H 7.79%, N 16.85%, Cl 18.28%). The proton NMR, as measured in deuteromethanol, shows characteristic signals at $\delta = 1.4–1.9$ (CH$_2$x5), 2.03 (COCH$_3$), 2.18 (CH$_2$), 2.59 (CH$_2$), 2.9–3.4 (NCH$_2$x5), 5.22 (CH), 5.51 (CH).

(3) The hydrochloride of 3-O-propionyl derivative of GHA-GS (briefly 3-O-propionyl-GHA-GS) is a colorless hygroscopic powder having no distinctly determinable melting point. It shows an optical rotation of $[\alpha]_D^{25} = +2° \pm 2°$ (c, 1 water). The elementary analysis coincides with the theoretical calculated for $C_{20}H_{41}N_7O_5 \cdot 3HCl \cdot H_2O$ (C 40.93%, H 7.90%, N 16.71%, Cl 18.21%). The proton NMR, as measured in deuteromethanol, shows characteristic signals at $\delta = 1.10$ (CH$_3$), 1.4–1.9 (CH$_2$x5), 2.21 (CH$_2$), 2.32 (COCH$_2$), 2.54 (CH$_2$), 2.9–3.4 (NCH$_2$x5), 5.21 (CH), 5.45 (CH).

(4) The hydrochloride of 3-O-butyryl derivative of GHA-GS (briefly 3-O-butyryl-GHA-GS is a colorless powder having no distinctly determinable melting point. It shows an optical rotation of $[\alpha]_D^{25} = +3° \pm 2°$ (c, 1 water). The elementary analysis coincides with the theoretical calculated for $C_{21}H_{43}N_7O_5 \cdot 3HCl \cdot 1.5H_2O$ (C 41.35%, H 8.10%, N 16.07%, Cl 17.44%). The proton NMR, as measured in deuteromethanol, shows characteristic signals at $\delta = 0.99$ (CH$_3$), 1.4–1.9 (CH$_2$x6), 2.14 (CH$_2$), 2.29 (CH$_2$), 2.54 (CH$_2$), 2.9–3.4 (NCH$_2$x5), 5.24 (CH), 5.48 (CH).

(5) The hydrochloride of 3-O-isobutyryl derivative of GHA-GS (briefly 3-O-isobutyryl-GHA-GS) is a colorless powder having no distinctly determinable melting point. It shows an optical rotation of $[\alpha]_D^{25} = +3° \pm 2°$ (c, 1 water). The elementary analysis coincides with the theoretical calculated for $C_{21}H_{43}N_7O_5 \cdot 3HCl \cdot 1.5$ H$_2$O (C 41.35%, H 8.10%, N 16.07%, Cl 17.44%). The proton NMR, as measured in deuteromethanol, shows characteristic signals at $\delta = 1.13$ (CH$_3$x2), 1.4–1.9 (CH$_2$x5), 2.15 (CH$_2$), 2.56 (CH$_2$), 2.59 (CH$_2$), 2.60 (CH), 2.9–3.4 (NCH$_2$x5), 5.25 (CH), 5.48 (CH).

(6) The hydrochloride of 3-O-pentanoyl derivative of GHA-GS (briefly 3-O-pentanoyl-GHA-GS) is a colorless powder having no distinctly determinable melting point. It shows an optical rotation of $[\alpha]_D^{25} = +1° \pm 2°$ (c, 1 water). The elementary analysis coincides with the theoretical calculated for $C_{22}H_{45}N_7O_5 \cdot 3HCl \cdot 1.5$ H$_2$O (C 42.34%, H 8.24%, N 15.71%, Cl 17.04%). The proton NMR, as determined in deuteromethanol, shows characteristic signals at $\delta = 0.91$ (CH$_3$), 1.2–1.9 (CH$_2$x7), 2.23 (CH$_2$), 2.30 (CH$_2$), 2.55 (CH$_2$), 2.58 (CH$_2$), 2.9–3.4 (NCH$_2$x5), 5.20 (CH), 5.25 (CH), 5.47 (CH).

(7) The hydrochloride of 3-O-hexanoyl derivative of GHA-GS (briefly 3-O-hexanoyl-GHA-GS) is a colorless powder having no distinctly determinable melting point. It shows an optical rotation of $[\alpha]_D^{25} = +4° \pm 2°$ (c, 1 water). The elementary analysis coincides with the theoretical calculated for $C_{23}H_{47}N_7O_5 \cdot 3HCl \cdot 1.5H_2O$ (C 43.29%, H 8.3%, N 15.37%, Cl 16.67%). The proton NMR, as measured in deuteromethanol, shows characteristic signals at $\delta=0.91$ (CH$_3$), 1.1–2.0 (CH$_2$ x 8), 2.26 (CH$_2$), 2.33 (CH$_2$), 2.58 (CH$_2$), 2.63 (CH$_2$), 2.9–3.4 (NCH$_2$x5), 5.20 (CH), 5.30 (CH).

(8) The hydrochloride of 3-O-octanoyl derivative of GHA-GS (briefly 3-O-octanoyl-GHA-GS) is a colorless powder having no distinctly determinable melting point. It shows an optical rotation of $[\alpha]_D^{25}=+3°\pm2°$ (c, 1 water). The elementary analysis coincides with the theoretical calculated for C$_{25}$H$_{51}$N$_7$O$_5$.3HCl.1.5H$_2$O (C 45.08%, H 8.63%, N 14.72%, Cl 15.97%). The proton NMR, as determined in deuteromethanol shows characteristic signals at $\delta=0.89$ (CH$_3$), 1.1–2.0 (CH$_2$x10), 2.22 (CH$_2$), 2.32 (CH$_2$), 2.66 (CH$_2$), 2.9–3.4 (NCH$_2$x5), 5.23 (CH), 5.49 (CH).

(9) The hydrochloride of 3-O-decanoyl derivative of GHA-GS (briefly 3-O-decanoyl-GHA-GS) is a colorless powder having no strictly determinable melting point. It shows an optical rotation of $[\alpha]_D^{25}=+3°\pm2°$ (c, 1 water). The elementary analysis coincides with the theoretical calculated for C$_{27}$H$_{55}$N$_7$O$_5$.3HCl.1.5H$_2$O (C 46.72%, H 8.86%, N 14.12%, Cl 15.32%). The proton NMR, as determined in deuteromethanol shows characteristic signals at $\delta=0.89$ (CH$_3$), 1.1–2.0 (CH$_2$ x 12), 2.26 (CH$_2$), 2.31 (CH$_2$), 2.59 (CH$_2$), 2.9–3.4 (NCH$_2$ x 5), 5.24 (CH), 5.50 (CH).

(10) The hydrochloride of 3-O-tetradecanoyl derivative of GHA-GS (briefly 3-O-tetradecanoyl-GHA-GS) is a colorless powder having no distinctly determinable melting point. It shows an optical rotation of $[\alpha]_D^{25}=+4°\pm2°$ (c, 1 water). The elementary analysis coincides with the theoretical calculated for C$_{31}$H$_{63}$N$_7$O$_5$.3HCl.1.5H$_2$O (C 49.63%, H 9.27%, N 13.07%, Cl 14.18%). The proton NMR, as determined in deuteromethanol, shows characteristic signals at $\delta=0.89$ (CH$_3$), 1.2–2.1 (CH$_2$x16), 2.1–2.4 (CH$_2$ x 2), 2.56 (CH$_2$), 2.9–3.4 (NCH$_2$ x 5), 5.25 (CH), 5.50 (CH).

(11) The hydrochloride of 3-O-benzoyl derivative of GHA-GS (briefly 3-O-benzoyl-GHA-GS) is a colorless powder having no distinctly determinable melting point. It shows an optical rotation of $[\alpha]_D^{25}=-5°\pm2°$ (c, 1 water). The elementary analysis coincides with the theoretical calculated for C$_{24}$H$_{41}$N$_7$O$_5$.3HCl.1.5H$_2$O (C 44.76%, H 7.36%, N 15.22%, Cl 16.51%). The proton NMR shows characteristic signals at $\delta=1.4$–1.9 (CH$_2$ x 5), 2.16 (CH$_2$), 2.72 (CH$_2$), 2.9–3.4 (NCH$_2$ x 5), 5.37 (CH), 5.52 (CH), 7.3–8.2 (COC$_6$H$_5$).

(II) Biological Properties

The antitumor activities of GHA-GS and 3-O-acyl derivatives thereof (all in the form of hydrochloride) against the mouse leukemia L1210 are as shown in the following table indicating a marked effect for prolonging the survival period. In the test, a group of five male BDF$_1$ strain mice (6 weeks of age) was inoculated intraperitoneally with 10$^5$ L1210 cells, and immediately thereafter each mouse was administered intraperitoneally with a physiological saline solution of the sample once a day for 6 consecutive days to determine the prolongation rate of survival period according to the equations:

Percentage life prolongation=(T/C)×100
T/C=(mean survival time of treated group)/(mean survival time of untreated group).

Curative Effect for Mouse Leukemia L1210

| Sample | Dose (mg/kg/day) | Prolongation rate of survival period (T/C) × 100 | Number of mice survived for 30 days |
|---|---|---|---|
| GHA-GS | 1.56 | 115 | 0 |
|  | 3.13 | >254 | 1 |
|  | 6.25 | >341 | 3 |
|  | 12.5 | >405 | 4 |
|  | 25 | >351 | 2 |
|  | 50 | >365 | 2 |
| 3-O—acetyl GHA-GS | 1.56 | 110 | 0 |
|  | 3.13 | >332 | 2 |
|  | 6.25 | >411 | 4 |
|  | 12.5 | >411 | 4 |
|  | 25 | >340 | 3 |
|  | 50 | 260 | 0 |
| 3-O—propionyl GHA-GS | 1.56 | 275 | 0 |
|  | 3.13 | >300 | 2 |
|  | 6.25 | >400 | 4 |
|  | 12.5 | >400 | 4 |
|  | 25 | >336 | 3 |
|  | 50 | 125 | 0 |
| 3-O—butyryl GHA-GS | 1.56 | 113 | 0 |
|  | 3.13 | >280 | 2 |
|  | 6.25 | >400 | 2 |
|  | 12.5 | >400 | 3 |
|  | 25 | >394 | 2 |
|  | 50 | toxic | 0 |
| 3-O—isobutyryl GHA-GS | 1.56 | 113 | 0 |
|  | 3.13 | 167 | 0 |
|  | 6.25 | >380 | 2 |
|  | 12.5 | 340 | 0 |
|  | 25 | toxic | 0 |
|  | 50 | toxic | 0 |
| 3-O—pentanoyl GHA-GS | 1.56 | 113 | 0 |
|  | 3.13 | 167 | 0 |
|  | 6.25 | >347 | 2 |
|  | 12.5 | >473 | 2 |
|  | 25 | 273 | 0 |
|  | 50 | 300 | 0 |
| 3-O—hexanoyl GHA-GS | 1.56 | 109 | 0 |
|  | 3.13 | 135 | 0 |
|  | 6.25 | 243 | 0 |
|  | 12.5 | >340 | 2 |
|  | 25 | 302 | 0 |
|  | 50 | 269 | 0 |
| 3-O—octanoyl GHA-GS | 1.56 | 128 | 0 |
|  | 3.13 | 192 | 0 |
|  | 6.25 | 199 | 0 |
|  | 12.5 | >302 | 1 |
|  | 25 | >345 | 2 |
|  | 50 | >302 | 1 |
| 3-O—decanoyl GHA-GS | 1.56 | 115 | 0 |
|  | 3.13 | 115 | 0 |
|  | 6.25 | 135 | 0 |
|  | 12.5 | 210 | 0 |
|  | 25 | 203 | 0 |
|  | 50 | 385 | 0 |
| 3-O—tetradecanoyl GHA-GS | 1.56 | 97 | 0 |
|  | 3.13 | 111 | 0 |
|  | 6.25 | 125 | 0 |
|  | 12.5 | 139 | 0 |
|  | 25 | 185 | 0 |
|  | 50 | toxic | 0 |
| 3-O—benzoyl GHA-GS | 1.56 | 100 | 0 |
|  | 3.13 | 100 | 0 |
|  | 6.25 | 107 | 0 |
|  | 12.5 | 125 | 0 |
|  | 25 | toxic | 0 |
|  | 50 | toxic | 0 |

Since the toxicity of GHA-GS or any of its 3-O-acyl derivatives is comparatively low, they may be used as effective anti-tumor agents for inhibiting mammalian tumors. Particularly, GHA-GS and 3-O-C$_{2-4}$-acyl derivatives thereof are highly effective, the percentage life prolongation being high and the number of mice survived for 30 days being large. For this purpose they are administered systemically to a mammal bearing a tumor in substantially non-toxic anti-tumor effective amount.

Since GHA-GS and 3-O-acyl derivatives thereof of this invention are unstable in the form of free base, it is desirable to convert them into the form of any non-toxic acid addition salt in a known manner by adding a pharmacologically acceptable acid. The acids to be added are inorganic acids such as hydrochloric acid, sulfuric acid, phosphoric acid, and boric acid and organic acids such as acetic acid, citric acid, tartaric acid, and glutaric acid. Of these acids, particularly preferred are hydrochloric acid, sulfuric acid, and tartaric acid.

According to this invention, GHA-GS or a 3-O-acyl derivative thereof represented by the general formula (I)

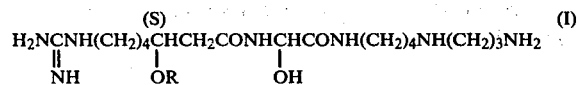

(wherein R represents a hydrogen atom, an alkanoyl group of 1 to 14 carbon atoms or an arylcarbonyl group) is prepared by heating in the presence of an acid catalyst, such as an inorganic or organic acid, (S)-7-guanidino-3-hydroxyheptanamide or a 3-O-acyl derivative represented by the general formula (II)

(wherein R is as defined above) and N-[4-[(3-aminopropyl)amino]butyl]-2,2-dihydroxyethanamide of the formula (III)

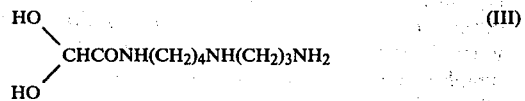

The latter substance of formula III is the subject of our copending application Ser. No. 375,916 filed herewith (Japanese Application No. 73510/81 filed May 18, 1981).

The condensation of a compound of formula (II) with a compound of formula (III) is allowed to proceed without having the active groups present in the reactants (such as guanidino group, amino group and hydroxyl group) protected with specific protective groups. Since the condensation is a water-liberating reaction, it is generally preferable to allow the reaction to proceed in an anhydrous solvent, but in view of the solubilities of reactant compounds of formulas (II) and (III), it is also possible to carry out the reaction in the presence of a small quantity of water in addition to an acid catalyst. Suitable acid catalysts include inorganic acids such as hydrochloric acid, sulfuric acid, and boric acid, and organic acids such as acetic acid, citric acid, tartaric acid, succinic acid, glutaric acid, and adipic acid. It is preferable to use a dicarboxylic acid such as glutaric acid. The amount of the acid to be used is 0.5 to 10, preferably 0.5 to 4.0 moles per mole of the compound of the formula (II). The amount of water to be added should be a least possible amount sufficient to dissolve the compounds of formulas (II) and (III) and the acid and to permit stirring of the reactant mixture. Water is used generally in an amount of 4 to 40 moles per mole of the compound of formula (II). The reaction temperature is 30° to 70° C., preferably 40° to 60° C. The reaction time depends on the reaction temperature but is preferably 1 to 2 days in view of the yield.

In synthesizing a 3-O-acyl-GHA-GS, on of the starting materials (S)-7-guanidino-3-acyloxyheptanamide represented by the general formula (II')

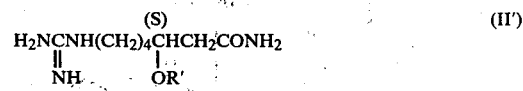

(where R' is an alkanoyl group of 1 to 14 carbon atoms or an arylcarbonyl group) is prepared by the direct acylation of the hydroxyl group of (S)-7-guanidino-3-hydroxyheptanamide of formula (II) (where R is a hydrogen atom). The acylation is conducted in anhydrous pyridine or a mixture of anhydrous pyridine and anhydrous dimethylformamide, using an acid chloride or an acid anhydride, at a reaction temperature of 0° to 80° C.

The (S)-7-guanidino-3-hydroxyheptanamide of the formula (II")

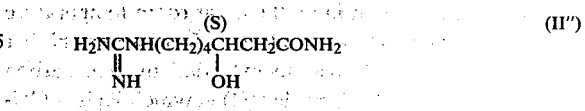

which is the same as the formula (II) when R is a hydrogen atom, is synthesized from L-lysine by converting it into (S)-3,7-diaminoheptanoic acid by the Arndt-Eistert method [Journal of Organic Chemistry, Vol. 17, 347 (1952)], deaminating the β-amino group with nitric acid, then converting the carboxyl group into amide, and converting the amino group into guanidino group. The whole procedure is described below in detail.

The two amino groups of L-lysine of the formula (IV)

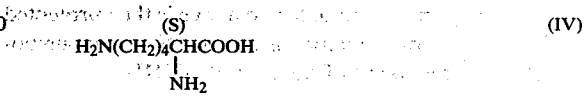

are protected with amino-protective groups to form a derivative having protected amino groups of the formula (V)

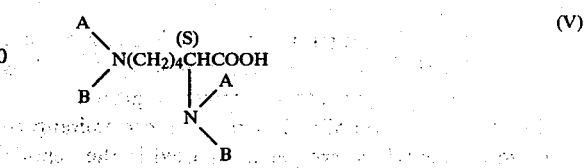

wherein A is a hydrogen atom and B is a monovalent amino-protective group or, alternatively, A and B jointly form a divalent amino-protective group. For the protection of amino group, those amino-protective groups which are generally used in the peptide synthesis may be utilized, but it is preferable in the present case to use a phthaloyl group as a divalent amino-protective group. The introduction of phthaloyl group into the two amino groups of L-lysine is carried out in a customary manner by the reaction with an excess of N-ethoxycarbonylphthalimide in an aqueous solution.

The carboxyl group of the amino-protected derivative (protected with phthaloyl groups in the present case) is converted into acyl chloride to form a compound of the formula (VI)

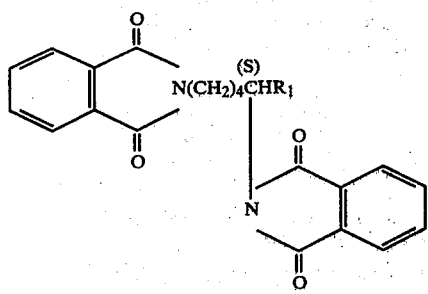

wherein $R_1$ is —COCl. This conversion is effected in a customary manner by using thionyl chloride or oxalyl chloride. The above phthaloyl compound of formula (VI) is then treated in ether with diazomethane to introduce a diazomethyl group, forming a compound of formula (VI) in which $R_1$ is —COCHN$_2$. This compound is then treated in methanol at room temperature with silver benzoate as catalyst to form a next higher homologous acid derivative extended by one carbon chain [an ester of the formula (VI) in which $R_1$ is —CH$_2$COOCH$_3$] (Arndt-Eistert synthesis). This compound is then removed of the amino-protective group and carboxyl-protective group to obtain (S)-3,7-diaminoheptanoic acid of the formula (VII)

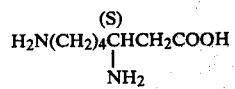

The amino group at 7-position of the (S)-3,7-diaminoheptanoic acid obtained above is then protected with an amino-protective group to form an amino-protected compound of the formula (VIII)

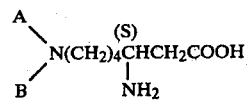

wherein A is a hydrogen atom and B is a monovalent amino-protective group or, alternatively, A and B jointly form a divalent amino-protective group.

For the protection of amino group, those amino-protective groups which are generally used in the peptide synthesis may be utilized as described before, but it is convenient in the present case to use a benzyloxycarbonyl group or tert-butoxycarbonyl group which is easily removed afterwards. Because the reactivity of the primary amino group at 7-position is higher than that of the secondary amino group at 3-position, it is possible to obtain preferentially a compound having its amino group at 7-position protected when the amount of an acylating agent used for the protection is restricted to one equivalent. Preferable acylating agents are an acid azide and an active ester which are known compounds.

The amino group at 3-position is then deaminated to obtain a 3-hydroxyl derivative of the formula (IX)

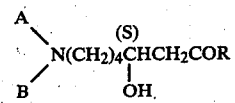

wherein A and B are as defined above and R is —OH. The deamination is effected in a customary manner in an aqueous acetic acid solution using a nitrite to obtain a 3-hydroxyl derivative with retention of the configuration. The 3-hydroxyl derivative is treated in ether with diazomethane to convert it into a methyl ester of the formula (IX) in which R is —OCH$_3$. The methyl ester is converted into an amide of the formula (IX) in which R is —NH$_2$. Then, the amino-protective group is removed to obtain (S)-7-amino-3-hydroxyheptanamide of the formula (X)

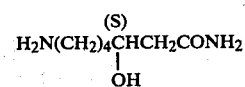

The amino group at the 7-position of the above heptanamide is then converted into a guanidino group to prepare (S)-7-guanidinohydroxyheptanamide of the formula (II'')

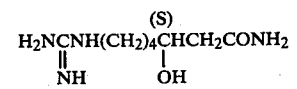

The conversion of the amino group at 7-position into the guanidino group is effected by the reaction with one equivalent of 2-methyl-1-nitroisourea or S-methylthiourea in an alkaline aqueous solution. For example, when the former compound is used, the nitro group which protects the guanidino group may be easily split off by the customary hydrogenolysis using a palladium or platinum catalyst.

Another reactant for the synthesis of the present carcinostatic compound, that is, N-[4-[(3-aminopropyl)amino]butyl]-2,2-dihydroxyethanamide of the formula (III)

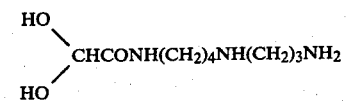

is synthesized from the starting material of the formula (XI)

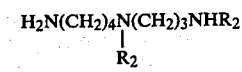

(wherein $R_2$ represents an amino-protective group) by acylating the free amino group with a dialkylacetal [formula (XII)], which is glyoxylic acid having its aldehyde group protected,

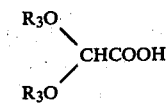

(where $R_3$ is an alkyl group of 1 to 5 carbon atoms) or a reactive derivative of carbonyl group thereof, and then removing the amino-protective group and the aldehyde-protective group. The whole procedure is described below in detail.

The starting compound of the formula (XI) is prepared by condensing in a customary manner a monoamino-protected 1,4-butanediamine of the formula (XIII)

$$R_4NH(CH_2)_4NH_2 \qquad (XIII)$$

(where $R_4$ represents an amino-protective group different from the above-mentioned $R_2$) with an amino-protected 3-halopropanamine of the formula (XIV)

$$X(CH_2)_3NHR_2 \qquad (XIV)$$

(where $R_2$ is the same amino-protective group as above and X is a halogen atom) to form a compound of the formula (XV)

$$R_4NH(CH_2)_4NH(CH_2)_3NHR_2 \qquad (XV)$$

(where $R_2$ and $R_4$ are amino-protective groups different from each other), then protecting the remaining imino group with the same amino-protective group as $R_2$, and selectively removing another amino-protective group $R_4$ to obtain the compound of above formula (XI).

Alternatively, the compound of the formula (XV) is obtained by condensing monoamino-protected 1,3-propanediamine of the formula (XVI)

$$R_2HN(CH_2)_3NH_2 \qquad (XVI)$$

(where $R_2$ is as defined above) with an amino-protected 4-halobutanamine of the formula (XVII)

$$X(CH_2)_4NHR_4 \qquad (XVII)$$

(where $R_4$ and X are as defined above) in a manner similar to that described above.

In the above synthetic procedures, for the protection of amino groups, those amino-protective groups which are customarily used in the peptide synthesis can be utilized, but the amino-protective group of $R_4$ should be selectively removable, leaving behind the amino-protective group of $R_2$. Accordingly, a combination of a benzyloxycarbonyl group removable by hydrogenolysis and a tert-butoxycarbonyl group removable by the weak acid treatment is a most preferable example. Either one of this pair may be $R_2$ or $R_4$.

The condensation of a compound of formula (XIII) with a compound of formula (XIV) or the condensation of a compound of formula (XVI) with a compound of formula (XVII) is easily conducted in an anhydrous solvent such as dimethylformamide at room temperature in the presence of triethylamine. The halogen in the compound of formulas (XIV) and (XVII) is preferably bromine. The dialkylacetal of glyoxylic acid of formula (XII),

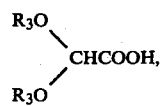

is easily formed by reacting glyoxylic acid with an alkanol using an acid catalyst in a customary manner. It is also conveniently formed by the alkaline hydrolysis of commercial ethyl 2,2-diethoxyacetate.

The acylation of the amino group of the compound of formula (XI) with a compound of formula (XII) is carried out by the procedure used in forming an ordinary amide linkage by using, for example, an acyl halide, acid azide, active ester, or acid anhydride. The removal of an amino-protective group and an aldehyde-protective group of the condensation product is generally performed by the weak acid hydrolysis. For instance, when the amino-protective group is a tert-butoxycarbonyl group and the aldehyde-protective group is diethylacetal, the condensation product is hydrolyzed in an aqueous dioxane solution by adding 2 to 3 equivalents of dilute hydrochloric acid and heating at 100° C. for 2 to 5 hours to form the hydrochloride of N-[4-(3-aminopropyl)aminobutyl]-2,2-dihydroxyethanamide of formula (III). When the amino-protective group is a benzyloxycarbonyl group, it is preferred to utilize hydrogenolysis with palladium or platinum oxide.

The present invention is is illustrated below with reference to Procedures and Examples, but the invention is not limited thereto.

Procedure 1. Synthesis of (S)-7-guanidino-3-hydroxyheptanamide (a) Synthesis of (S)-3,7-diaminoheptanoic acid Into 150 ml of water, was dissolved 15 g (82.15 mmoles) of L-lysine hydrochloride followed by 8.7 g (82.15 mmoles) of sodium carbonate and 43.2 g (200 mmoles) of N-ethoxycarbonylphthalimide. The mixture was stirred for 20 hours at room temperature and the reaction mixture was washed with 50 ml of ethyl acetate. The aqueous layer was adjusted to pH 3.0 with 6 N hydrochloric acid, and extracted three times with 100 ml of toluene. The extract was washed twice with 100 ml of water which had been adjusted to pH 2.0, dried over anhydrous sodium sulfate, and evaporated to dryness under reduced pressure to obtain 27.95 g (84% yield) of a white powder of di-N,N-phthaloyl-L-lysine. Decomp. point, 72°–72° C.; $[\alpha]_D^{22} -32°$ (c, 1 methanol).

To 27.0 g (66.4 mmoles) of di-N,N-phthaloyl-L-lysine, was added 40 ml of oxalyl chloride. To the mixture heated in an oil bath at 90° C., was added 40 ml of 1,2-dimethoxyethane. The mixture was further heated under reflux for 2 hours. The reaction mixture was evaporated to dryness, dissolved again in 20 ml of 1,2-dimethoxyethane and added dropwise to 500 ml of an ether solution of diazomethane (330 mmoles) while cooling in ice. The mixture was further stirred for one hour. The reaction mixture was evaporated to dryness, dissolved in 250 ml of anhydrous methanol, admixed with a solution of 3.4 g (14.8 mmoles) of silver benzoate in 50 ml of triethylamine, and stirred for 15 hours at room temperature. The precipitate was collected by filtration, dissolved in 100 ml of chloroform, freed from the insolubles by filtration, and evaporated to dryness to obtain 15.3 g (53% yield) of methyl (S)-3,7-diphthaloylaminoheptanoate. Decomp. point, 118°–119° C.; $[\alpha]_D^{22} -3°$ (c, 2 chloroform).

To 15.0 g (34.5 mmoles) of methyl (S)-3,7-diphthaloylaminoheptanoate, were added 100 ml of a 1 M alcoholic hydrazine hydrate and 100 ml of 95% ethanol. The mixture was heated under reflux for one hour (at an oil bath temperature of 90° C.). The reaction mixture was evaporated to dryness, dissolved in 250 ml of 5-% hydrochloric acid, heated at 80° C. for one hour, adjusted to pH 7.1 with 17% aqueous ammonia, and passed through a column (27 mm in inner diameter) packed with 300 ml of Amberlite ® CG-50 (70% NH₄-type). The column was washed with each 900 ml of water and 0.2 M aqueous ammonia, and eluted with 0.5 M aqueous ammonia. The fractions positive to ninhydrin test were collected and evaporated to dryness to obtain 3.15 g (57% yield) of (S)-3,7-diaminoheptanoic acid ($C_7H_{16}N_2O_2 \cdot 1/4H_2CO_3$). $[\alpha]_D^{21} +29°$ (c, 1 water)

(b) Synthesis of (S)-7-guanidino-3-hydroxyheptanamide

Into 30 ml of a pyridine-water-triethylamine (10:10:1 by volume) mixture, was dissolved 3.1 g (19.3 mmoles) of (S)-3,7-diaminoheptanoic acid obtained in (a) above. To the resulting solution, was added gradually 4.81 g (19.3 mmoles) of N-benzyloxycarbonyloxysuccinimide. The mixture was stirred at room temperature for 5 hours. The reaction mixture was evaporated to dryness, dissolved in 30 ml of water, adjusted to pH 6.4 with 6 N hydrochloric acid, then passed through a column (16 mm in inner diameter) packed with 100 ml of Amberlite ® CG-50 (80% NH₄-type), and developed with 300 ml of water. The effluent was collected and passed through a column (16 mm in inner diameter) packed with 100 ml of Dowex ®50 W-X4 (H-type). The column was washed with each 300 ml of water and 0.2 M aqueous ammonia, and eluted with 0.5 M aqueous ammonia (10 ml fractions). The fraction Nos. 16 to 33 were combined and evaporated to dryness to obtain 2.73 g (48% yield) of a white powder of (S)-3-amino-7-benzyloxycarbonylaminoheptanoic acid ($C_{15}H_{22}N_2O_4 \cdot H_2O$). Decomp. point 143°-147° C.; $[\alpha]_D^{22} +14°$ (c, 1 methanol). The above-said column of Amberlite ® CG-50 was eluted with 0.5 M aqueous ammonia to recover 746 mg (24% recovery) of (S)-3,7-diaminoheptanoic acid.

Into 50 ml of 33% aqueous acetic acid solution, was dissolved 2.7 g (9.17 mmoles) of (S)-3-amino-7-benzyloxycarbonylaminoheptanoic acid. To the solution, while being cooled in ice, was added slowly over a period of one hour a solution of 1.9 g (27.51 mmoles) of sodium nitrite in 10 ml of water. The mixture was stirred for one hour and left standing for 24 hours at 5° C. The reaction mixture was diluted with 50 ml of water and extracted twice with 50 ml of ethyl acetate. The extract was dried with anhydrous sodium sulfate and evaporated to dryness to obtain 2.16 g of a crude powder. The crude powder was subjected to column chromatography using a column (28 mm in inner diameter) packed with 200 g of silica gel (Wako Gel ® C-200) and a chloroform-methanol-concentrated ammonia (30:10:1 by volume) mixture as developing solvent. Fraction Nos. 51 to 60 (each 20 ml in volume) were combined and evaporated to dryness to obtain 460 mg (17% yield) of a white powder of (S)-7-benzyloxycarbonylamino-3-hydroxyheptanoic acid. Decomposition point, 115°-117° C.; $[\alpha]_D^{23} +3°$ (c, 2 methanol).

Into 4 ml of 1,2-dimethoxyethane, was dissolved 450 mg (1.52 mmoles) of (S)-7-benzyloxycarbonylamino-3-hydroxyheptanoic acid. To the solution, while being cooled in ice, was added dropwise 7 ml (4.56 mmoles) of an ether solution of diazomethane. The mixture was stirred for 30 minutes and then evaporated to dryness to yield 461 mg (98% yield) of methyl (S)-7-benzyloxycarbonylamino-3-hydroxyheptanoate. $[\alpha]_D^{21} +1°$.

Into 50 ml of anhydrous methanol, was dissolved 450 mg (1.45 mmoles) of methyl (S)-7-benzyloxycarbonylamino-3-hydroxyheptanoate. The solution, cooled at $-10°$ C., was saturated with gaseous ammonia and left standing in a sealed tube for 3 days at room temperature. The reaction mixture was evaporated to dryness and subjected to chromatography using a column (20 mm in inner diameter) packed with 50 g of silica gel (Wako Gel ® C-200) and a chloroform-methanol (100:1 by volume) mixture as developing solvent. Fraction Nos. 82 to 106 (each 10 ml in volume) were combined and evaporated to dryness to yield 371 mg (87% yield) of a white powder of (S)-7-benzyloxycarbonylamino-3-hydroxyheptanamide. Decomp. point, 126°-127° C.; $[\alpha]_D^{22} -3°$ (c, 5 methanol).

Into a mixture of 10 ml of 90% aqueous methanol and 0.01 ml of acetic acid, was dissolved 350 mg (1.19 mmoles) of (S)-7-benzyloxycarbonylamino-3-hydroxyheptanamide. After addition of 50 mg of 5% palladium-carbon, the mixture was stirred under a hydrogen stream for 3 hours at room temperature. After removal of the catalyst by filtration, the filtrate was evaporated to dryness, then dissolved again in a small volume of water, and passed through a column (12 mm in inner diameter) packed with 30 ml of Dowex ® 50 W-X4 (H-type). The column was then washed with 90 ml of water and eluted with 0.5 M aqueous ammonia. Fraction Nos. 28 to 34 (each 3 ml in volume) were combined and evaporated to dryness to obtain 201 mg (96% yield) of (S)-7-amino-3-hydroxyheptanamide. $[\alpha]_D^{22} -2°$ (c, 2 water).

Into 3 ml of water, was dissolved 190 mg (1.08 mmoles) of (S)-7-amino-3-hydroxyheptanamide followed by 0.54 ml of 2 N aqueous sodium hydroxide solution. To the solution, while being cooled in ice, was added dropwise over a period of 30 minutes 1 ml of a methanol solution containing 129 mg (1.08 mmoles) of 2-methyl-1-nitrosourea. The mixture was further stirred for 5 hours. The reaction mixture was adjusted to pH 6.0 with 6 N hydrochloric acid, then evaporated to dryness, and purified by chromatography using a column (15 mm in inner diameter) packed with 30 g of silica gel (Wako Gel ® C-200) and a mixture of chloroform-methanol-concentrated aqueous ammonia (60:10:1 by volume) as the developing solvent. Fraction Nos. 67 to 90 (each 6 ml in volume) were combined and evaporated to dryness to obtain 187 mg (70% yield) of a white powder of (S)-7-nitroguanidino-3-hydroxyheptanamide. Decomp. point, 148°-149° C.; $[\alpha]_D^{22} -2°$ (c, 2 methanol).

Into a mixture of 15 ml of water, 15 ml of methanol and 7.5 ml of acetic acid, was dissolved 170 mg (0.69 mmole) of (S)-7-nitroguanidino-3-hydroxyheptanamide. After addition of 50 mg of 5% palladium-carbon, the mixture was stirred under a hydrogen stream for one hour at room temperature. After removal of the catalyst by filtration, the filtrate was evaporated to dryness to obtain 165 mg of a crude powder. This powder was dissolved in 10 ml of water, passed through a column (12 mm in inner diameter) packed with 20 ml of CM-Sephadex ® C-25 (Na-type), and eluted with 0.5 M sodium chloride solution. Fraction Nos. 18 to 25 (each 2 ml in volume) were combined and evaporated to dryness. The dried substance was extracted three times with 10 ml of methanol. The methanol extracts were combined, passed through a column (20 mm in inner diameter) packed with 100 ml of Sephadex ® LH-20, and developed with methanol. Fraction Nos. 28 to 46 (each 1 ml in volume) were combined and evaporated to dryness to obtain 149 mg (91% yield) of a white powder of (S)-7-guanidino-3-hydroxyheptanamide hydrochloride ($C_8H_{18}N_4O_2 \cdot HCl$). $[\alpha]_D^{22} -2°$ (c, 2 water.

Procedure 2. Synthesis of N-[4-(3-aminopropyl)aminobutyl]-2,2-dihydroxyethanamide.

(a) Synthesis of mono-N-benzyloxycarbonyl-1,4-butanediamine

Into 30 ml of 50% aqueous methanol, was dissolved 1.76 g (20 mmoles) of 1,4-butanediamine followed by the addition of 5.48 g (20 mmoles) of benzyl-S-4,6-dimethylpyrimido-2-yl thiocarbonate (produced by Kokusan Kagaku Co.) After stirring for 3 hours, the reaction mixture was filtered to remove the precipitate [2.08 g (28%) of di-N-benzyloxycarbonyl compound was separated]. The filtrate was evaporated to dryness, dissolved in 250 ml of chloroform, and washed 5 times with 100 ml of water. The chloroform layer was dried over anhydrous sodium sulfate and evaporated to dryness to obtain 1.0 g (23% yield) of mono-N-benzyloxycarbonyl-1,4-butanediamine in colorless syrup form.

(b) Synthesis of O-tosyl-3-tert-butoxycarbonylamino-1-propanol

Into 30 ml of methanol, was dissolved 1.5 g (20 mmoles) of 3-amino-1-propanol followed by the addition of 4.8 g (20 mmoles) of S-tert-butoxycarbonyl-4,6-dimethyl-2-mercaptopyrimdine (a product of Kokusan Kagaku Co.). After stirring for 6 hours, the reaction mixture was evaporated to drynes, dissolved in 200 ml of chloroform, and washed with 200 ml of water. The chloroform layer was concentrated and subjected to column chromatography using 300 g of silica gel (Wako Gel® C-200) and a toluene-ethyl acetate (1:1 by volume) mixture as a developing solvent. The Fraction Nos. 82 to 151 (each 15 ml in volume) were combined and evaporated to obtain 2.95 g (84% yield) of 3-tert-butoxycarbonylamino-1-propanol in the form of colorless oil.

Into 50 ml of pyridine, was dissolved 2.95 g (16.9 mmoles) of 3-tert-butoxycarbonylamino-1-propanol. To this solution, while being cooled in ice under an argon atmosphere, was added dropwise over a period of 40 minutes a pyridine solution containing 3.36 g (17.7 mmoles) of p-toluenesulfonyl chloride. The mixture was left standing overnight at 7° C., admixed with a small quantity of water, and evaporated to dryness. The residue was dissolved in 200 ml of chloroform, washed successively with 5% aqueous potassium hydrogensulfate solution, saturated aqueous sodium hydrogencarbonate solution, and water, then dried over anhydrous sodium sulfate, evaporated to dryness, and subjected to column chromatography using 120 g of silica gel (Wako Gel® C-200) and a toluene-ethyl acetate (8:1 by volume) mixture as a developing solvent. The Fraction Nos. 35 to 68 (each 15 ml in volume) were combined and evaporated to dryness to obtain 3.06 g (55% yield) of O-tosyl-3-tert-butoxycarbonylamino-1-propanol in the form of colorless oil.

(c) Synthesis of N-tert-butoxycarbonyl-N-(tert-butoxycarbonylaminopropyl)-1,4-butanediamine Into 15 ml of dimethylformamide, was dissolved 800 mg (2.43 mmoles) of the O-tosyl-3-tert-butoxycarbonylamino-1-propanol obtained in (b) above. After addition of 510 mg (4.8 mmoles) of lithium bromide ($LiBr \cdot H_2O$), the mixture was stirred at room temperature for 24 hours. To the reaction mixture containing the bromo derivative, were added 540 mg (2.43 mmoles) of the mono-N-benzyloxycarbonyl-1,4-butanediamine obtained in (a) above and 0.34 ml of triethylamine. The resulting mixture was stirred at room temperature for 48 hours. To the reaction mixture, was added 699 mg (2.9 mmoles) of S-tert-butoxycarbonyl-4,6-dimethyl-2-mercaptopyrimidine. The mixture was stirred for 13 hours at room temperature. The reaction mixture was evaporated to dryness, dissolved in 100 ml of chloroform, washed with 50 ml of water, dried over anhydrous sodium sulfate, evaporated to dryness, and subjected to column chromatography using 200 g of silica gel (Wako Gel® C-200) and a toluene-ethyl acetate (4:1 by volume) mixture as a developing solvent. The Fraction Nos. 134 to 165 (each 12 ml in volume) were combined and evaporated to dryness to obtain 608 mg (52% yield) of N-benzyloxycarbonyl-N'-tert-butoxycarbonyl-N'-(tert-butoxycarbonylaminopropyl)-1,4-butanediamine in colorless syrup form.

Into 5 ml of methanol, was dissolved 144 mg (0.3 mmole) of the syrup-like substance obtained above. To the solution, was added 100 mg of 5% palladium-barium carbonate. The mixture was stirred under a hydrogen stream at room temperature for 5 hours. The catalyst was removed by filtration, and the filtrate was evaporated to dryness to obtain 103 mg (100% yield) of N-tert-butoxycarbonyl-N-(tert-butoxycarbonylaminopropyl)-1,4-butanediamine.

(d) Synthesis of N-[4-(3-aminopropyl)aminobutyl]-2,2-dihydroxyethanamide.

Into 2 ml of ethyl acetate, were dissolved 100 mg (0.29 mmole) of the N-tert-butoxycarbonyl-N-(tert-butoxycarbonylaminopropyl)-1,4-butanediamine obtained in (c) above and 148 mg (1 mmole) of 2,2-diethoxyacetic acid followed by the addition of 135 mg (1 mmole) of 1-hydroxybenztriazole and 206 mg (1 mmole) of dicyclohexylcarbodiimide. The mixture was stirred for 15 hours at room temperature. The precipitate was collected by filtration and washed with cold ethyl acetate. The filtrate and washing were combined and washed successively with 1 M aqueous ammonia and water. The ethyl acetate layer was dried over anhydrous sodium sulfate, evaporated to dryness, and subjected to column chromatography using 20 g of silica gel (Wako Gel® C-200) and a toluene-ethyl acetate (1:2 by volume) mixture as a developing solvent. The Fraction Nos. 14 to 21 (each 3 ml in volume) were combined and evaporated to dryness to obtain 109 mg (79% yield) of N-[4-(3-tert-butoxycarbonylaminopropyl)-4-tert-butoxycarbonylaminobutyl]-2,2-diethoxyethanamide in colorless syrup form.

Into 1 ml of dioxane, was dissolved 44 mg (0.13 mmole) of the above amide. After addition of 2.5 ml of 1 N hydrochloric acid, the mixture was stirred for 4 hours in an oil bath at 100° C. The reaction mixture was adjusted to pH 6 by neutralizing with 0.2 N sodium hydroxide solution, evaporated to dryness, and extracted with 1.5 ml of methanol. The methanol extract was passed through a column (16.5 mm in inner diameter) packed with 100 ml of Sephadex® LH-20, and developed with methanol. The Fraction Nos. 22 to 25 (each 2 ml in volume) which were positive to ninhydrin test were combined, and evaporated to dryness to obtain 13 mg (45% yield) of N-[4-(3-aminopropyl)aminobutyl]-2,2-dihydroxyethanamide dihydrochloride in colorless syrup form.

EXAMPLE 1. SYNTHESIS OF GHA-GS

A mixture of 51 mg (0.214 mmole) of (S)-7-guanidino-3-hydroxyheptanamide hydrochloride, 112 mg (0.385 mmole) of N-[4-(3-aminopropyl)aminobutyl]-2,2-dihydroxyethanamide dihydrochloride, 70 mg (0.53 mmole) of glutaric acid, and 0.07 ml (3.9 mmoles) of water was stirred for 43 hours at 60° C. The reaction mixture was admixed with 20 ml of 0.4 M sodium chloride solution, adjusted to pH 6.1 with 10% aqueous ammonia, and passed through a column (12 mm in inner diameter) packed with 20 ml of CM Sephadex® C-25 equilibrated with 0.4 M sodium chloride solution. The column was then subjected to gradient elution using each 80 ml of 0.4 M and 1.0 M sodium chloride solutions. The Fraction Nos. 41 to 50 (each 2 ml in volume) were combined, evaporated to dryness, and extracted three times with 10 ml of methanol. The methanol extract was passed through a column (20 mm in inner diameter) packed with 100 ml of Sephadex® LH-20, and developed with methanol. The Fraction Nos. 30 to 42 (each 1 ml in volume) were combined and evaporated to dryness to obtain 38.4 mg (35% yield) of a white powder of N-[4-(3-aminopropyl)aminobutyl]-2-[(S)-7-guanidino-3-hydroxyheptanamido]-2-hydroxyethanamide (GHS-GS) trihydrochloride.

EXAMPLE 2. SYNTHESIS OF 3-O-ACETYL-GHA-GS

To 813 mg of (S)-7guanidino-3-hydroxyheptanamide hydrochloride, were added 7 ml of pyridine and 7 ml of acetic anhydride. The mixture was stirred overnight at room temperature. The reaction mixture was admixed with 100 ml of ice water, concentrated under reduced pressure, and passed through a column (2.5 cm in inner diameter) packed with 450 ml of CM-Sephadex® C-25 (Na-type). Fractions obtained by the elution with sodium chloride solutions of 0.16 to 0.2 M were combined, evaporated to dryness under reduced pressure, and extracted with methanol. The methanol extract was passed through a column (5.6 cm in inner diameter) packed with 1.5 liters of Sephadex® LH-20 swollen with methanol, then the column was developed with methanol and desalted. The active fractions were combined and evaporated to dryness under reduced pressure to obtain 753 mg (78.8% yield) of a white powder of (S)-7-guanidino-3-acetoxyheptanamide hydrochloride. The proton nuclear magnetic resonance spectrum (NMR) of this hydrochloride, as measured in deuteromethanol using tetramethylsilane (TMS) as standard at 60 MHz, showed the following characteristic signals: 1.4–1.9 ($CH_2$x3), 2.00 ($COCH_3$), 2.49 ($CH_2$), 3.18 ($NCH_2$), and 5.19 (CH).

A mixture of 354 mg of (S)-7-guanidino-3-acetoxyheptanamide hydrochloride obtained above, 429 mg of N-[4-(3-aminopropyl)aminobutyl]-2,2-dihydroxyethanamide hydrochloride, and 333 mg of glutaric acid was dissolved in 0.5 ml of water, and heated overnight at 60° C. The reaction mixture was diluted with water and passed through a column of CM-Sephadex®. The fractions eluted with sodium chloride solutions of 0.52 to 0.56 M were collected and further purified and desalted by means of Sephadex® LH-20 to obtain 146 mg (21.6% yield) of 3-O-acetyl-GHA-GS trihydrochloride.

EXAMPLE 3. SYNTHESIS OF 3-O-PROPIONYL-GHA-GS

A mixture of 1.3 g of (S)-7-guanidino-3-hydroxyheptanamide hydrochloride, 5 ml of pyridine, and 5 ml of propionic anhydride was stirred for 2 hours at 60° C. The reaction mixture was diluted with ice water, concentrated under reduced pressure, and dissolved in 10 ml of 0.5 M aqueous sodium chloride solution. The resulting solution was passed through a column packed with Diaion® HP-20 which had been equilibrated with 0.5 M aqueous sodium chloride solution and washed successively with 0.5 M and 0.2 M aqueous sodium chloride solutions. The fractions eluted with water and 30% aqueous methanol were collected and concentrated under reduced pressure to obtain 1.26 g (78.5% yield) of (S)-7-guanidino-3-propionyloxyheptanamide hydrochloride in oily form. NMR: 1.10 ($CH_3$), 1.4 to 1.9 ($CH_2$x3), 2.32 ($COCH_2$), 2.51 ($CH_2$), 3.21 ($NCH_2$), 5.22 (CH).

To the above oily substance, were added 2.24 g of N-[4-(3-aminopropyl)aminobutyl]-2,2-dihydroxyethanamide hydrochloride, 1.4 g of glutaric acid, and 1.5 ml of water. The mixture was heated at 60° C. overnight. The reaction mixture was diluted with water and passed through a column of CM-Sephadex® C-25 (Na-type). Fractions eluted with 0.58 M to 0.65 M aqueous sodium chloride solutions were collected and passed through a column of Diaion® HP-20 equilibrated with 1 M aqueous sodium chloride solution. The column was washed successively with 1 M and 0.1 M aqueous sodium chloride solutions. The fractions obtained by the elution with water and 30% aqueous methanol were collected, evaporated to dryness under reduced pressure, and extracted with methanol. The methanol extract was treated with Sephadex® LH-20 in a manner similar to that in Example 2 to obtain 658 mg of a white powder of 3-O-propionyl-GHA-GS trihydrochloride.

EXAMPLE 4. SYNTHESIS OF 3-O-BUTYRYL-GHA-GS

Into 6.5 ml of dimethylformamide, was dissolved 676 mg of (S)-7-guanidino-3-hydroxyheptanamide hydrochloride followed by the addition of 1.9 ml of pyridine and 3.7 ml of n-butyric anhydride. The mixture was heated at 50° C for 24 hours. The reaction mixture was admixed with 20 ml of ice water, the separated oil layer was removed therefrom, and the aqueous layer was subjected to chromatography similarly to Example 2, using successively CM-Sephadex® C-25 and Sephadex® LH-20 to obtain 603 mg of (S)-7-guanidino-3-butyryloxyheptanamide hydrochloride. NMR: 0.92 ($CH_3$), 1.2–2.0 ($CH_2$x4), 2.28 ($COCH_2$), 2.50 ($CH_2$), 3.18 ($CH_2$), 5.24 (CH).

Into 0.5 ml of water, were dissolved 513 mg of the above compound, 592 mg of N-[4-(3-aminopropyl)aminobutyl]-2,2-dihydroxyethanamide hydrochloride, and 220 mg of glutaric acid. The solution was heated at 60° C. for 24 hours. The reaction mixture was diluted with water and subjected to chromatography, similarly to Example 2, using CM-Sepharex® C-25, Diaion® HP-20, and Sephadex® LH-20 to obtain 314 mg of a white powder of 3-O-butyryl-GHA-GS trihydrochloride.

EXAMPLE 5. SYNTHESIS OF 3-O-ISOBUTYRYL-GHA-GS

Into 4.5 ml of dimethylformamide, was dissolved 645 mg of (S)-7-guanidino-3-hydroxyheptanamide hydrochloride followed by the addition of 0.9 ml of pyridine and 3.6 ml of isobutyric anhydride. The mixture was heated at 50° C. for 24 hours. The reaction mixture was admixed with 20 ml of ice water, the separated oil layer was removed therefrom, and the aqueous layer was treated, similarly to Example 2, with CM-Sephadex ® C-25 and Sephadex ® LH-20 to obtain 729 mg of (S)-7-guanidino-3-isobutyryloxyheptanamide hydrochloride in oily form.

NMR: 1.13 ($CH_3$x2), 1.4–1.9 ($CH_3$x3), 2.50 ($CH_2$), 2.65 (COCH), 3.18 ($CH_2$), 5.24 (CH).

Into 0.5 ml of water, were dissolved 692 mg of the above oily substance, 821 mg of N-[4-(3-aminopropyl)aminobutyl]-2,2-dihydroxyethanamide, and 297 mg of glutaric acid. The solution was heated at 60° C. for 28 hours. The reaction mixture was treated as in Example 2 with CM Sephadex ® C-25, Diaion ® HP-20, and Sephadex ® LH-20 to obtain 389 mg of a white powder of 3-O-isobutyryl-GHA-GS trihydrochloride.

EXAMPLE 6. SYNTHESIS OF 3-O-PENTANOYL-GHA-GS

Into 4.5 ml of dimethylformamide, was dissolved 624 mg of (S)-7-guanidino-3-hydroxyheptanamide hydrochloride followed by the addition of 0.9 ml of pyridine and 4 ml of n-valeric anhydride. The solution was heated at 50° C. for 24 hours. The reaction mixture was admixed with 20 ml of ice water, the separated oil layer was removed therefrom, and the aqueous layer was treated, as in Example 2, with CM Sephadex ® C-25 and Sephadex ® LH-20 to obtain 582 mg of purified (S)-7-guanidino-3-pentanoyloxyheptanamide hydrochloride in oily form. NMR: 0.91 ($CH_3$), 1.2–1.9 ($CH_2$x5), 2.28 ($COCH_2$), 2.47 ($CH_2$), 3.14 ($CH_2$), 5.21 (CH).

Into 0.5 ml of water, were dissolved 551 mg of the above oily substance, 602 mg of N-[4-(3-aminopropyl)aminobutyl]-2,2-dihydroxyethanamide hydrochloride, and 226 mg of glutaric acid. The solution was heated at 60° C. for 28 hours. The reaction mixture was diluted with water and treated, as in Example 2, with CM Sephadex ® C-25, Diaion ® HP-20, and Sephadex ® LH-20 to obtain 282 mg of a white powder of purified 3-O-pentanoyl-GHA-GS trihydrochloride.

EXAMPLE 7. SYNTHESIS OF 3-O-HEXANOYL-GHA-GS

Into 4.5 ml of dimethylformamide, was dissolved 596 mg of (S)-7-guanidino-3-hydroxyheptanamide hydrochloride followed by the addition of 1.2 ml of pyridine and 3.9 ml of n-hexanoic anhydride. The solution was stirred under application of heat for 24 hours. The reaction mixture was admixed with 20 ml of ice water, left standing for 30 minutes, admixed with 20 ml of ethyl acetate, and left standing to effect phase separation. The ethyl acetate layer was extracted 4 times with 30 ml of 0.5 N hydrochloric acid. The aqueous layers were combined, neutralized with 2 N aqueous sodium hydroxide solution, concentrated under reduced pressure, desalted by treating with methanol, and treated, as in Example 2, with CM Sephadex ® C-25 and Sephadex ® LH-20 to obtain 653 mg of purified (S)-7-guanidino-3-hexanoyl-heptanamide hydrochloride in oily form. NMR: 0.89 ($CH_3$), 1.1–1.9 ($CH_2$x6), 2.36 ($COCH_2$), 2.45 ($CH_2$), 3.14 ($CH_2$), 5.17 (CH).

Into 0.5 ml of water, were dissolved 506 mg of the above oily substance, 525 mg of N-[4-(3-aminopropyl)aminobutyl]-2,2-dihydroxyethanamide hydrochloride, and 198 mg of glutaric acid. The solution was heated at 60° C. for 24 hours. The reaction mixture was diluted with water and treated, as in Example 2, with CM Sephadex ®, Diaion ® HP-20, and Sephadex ® LH-20 to to obtain 197.4 mg of a white powder of purified 3-O-hexanoyl-GHA-GS trihydrochloride.

EXAMPLE 8. SYNTHESIS OF 3-O-OCTANOYL-GHA-GS

Into 4.5 ml of dimethylformamide, was dissolved 610 mg of (S)-7-guanidino-3-hydroxyheptanamide hydrochloride followed by the addition of 1.2 ml of pyridine and 4.6 ml of n-octanoic anhydride. The solution was heated with stirring at 60° C. for 24 hours. The reaction mixture was admixed with 20 ml of ice water, left standing for 30 minutes, then admixed with 20 ml of ethyl acetate, and left standing to effect phase separation. The ethyl acetate layer was extracted 4 times with 30 ml of 0.5 N hydrochloride acid. The aqueous layers were combined, neutralized with 2 N aqueous sodium hydroxide solution, then concentrated under reduced pressure, and treated, as in Example 2, with CM Sephadex ® and Sephadex ® LH-20 to obtain 630 mg of purified (S)-7-guanidino-3-octanoyloxyheptanamide hydrochloride in oily form. NMR: 0.92 ($CH_3$), 1.1–1.9 ($CH_2$x8), 2.30 ($COCH_2$), 2.50 ($CH_2$), 3.20 ($CH_2$), 5.18 (CH).

Into 0.5 ml of water, were dissolved 514 mg of the above oily substance, 493 mg of N-[4-(3-aminopropyl)aminobutyl]-2,2-dihydroxyethanamide hydrochloride, and 186 mg of glutaric acid. The solution was heated at 60° C. for 24 hours. The reaction mixture was diluted with water and treated, as in Example 2, with CM Sephadex ®, Diaion ® HP-20 and Sephadex ® LH-20 to obtain 187.6 mg of a white powder of purified 3-O-octanoyl-GHA-GS trihydrochloride.

EXAMPLE 9. SYNTHESIS OF 3-O-DECANOYL-GHA-GS

Into 6.5 ml of dimethylformamide, was dissolved 603 mg of (S)-7-guanidino-3-hydroxyheptanamide hydrochloride followed by the addition of 0.82 ml of pyridine and 9.9 g of n-decanoic anhydride. The solution was stirred with heating at 60° C. for 48 hours. The reaction mixture was diluted with 20 ml of ice water, left standing for 30 minutes, and treated as in Example 8 to obtain 3.12 mg of (S)-7-guanidino-3-decanoyloxyheptanamide hydrochloride in oily form. NMR: 6.88 ($CH_3$), 1.1–1.9 ($CH_2$x10), 2.28 ($COCH_2$), 2.46 ($CH_2$), 3.16 ($CH_2$), 5.22 (CH).

Into 0.45 ml of water, were dissolved 275 mg of the above oily substance, 244 mg of N-[4-(3-aminopropyl)aminobutyl]-2,2-dihydroxyethanamide hydrochloride, and 93 mg of glutaric acid. The solution was heated at 60° C. for 24 hours. The reaction mixture was diluted with water and purified as in Example 2 by using CM Sephadex ®, Diaion ® HP-20 and Sephadex ® LH-20 to obtain 87 mg of a white powder of 3-O-octanoyl-GHA-GS trihydrochloride.

EXAMPLE 10. SYNTHESIS OF 3-O-TETRADECANOYL-GHA-GS

Into 7 ml of dimethylformamide, was dissolved 500 mg of (S)-7-guanidino-3-hydroxyheptanamide hydrochloride followed by the addition of 0.85 ml of pyridine and 4.6 g of n-tetradecanoic anhydride. The solution was heated with stirring at 80° C. for 20 hours. The reaction mixture was admixed with 50 ml of methanol, the precipitated excess n-tetradecanoic anhydride was removed by filtration, and the filtrate was concentrated under reduced pressure. The residue was dissolved in 10 ml of 1 N sodium hydroxide solution and extracted three times with 10 ml of n-butanol. The butanol layer was washed successively with 1 N hydrochloric acid, 1 N aqueous sodium hydroxide solution, and water. The butanol layer was then extracted with methanol and the methanol layer was concentrated under reduced pressure to yield 242 mg of a white residue which was further purified by using a Diaion® HP-20 column to obtain 145 mg of (S)-7-guanidino-3-tetradecanoyloxyheptanamide hydrochloride. NMR: 0.89 ($CH_3$), 1.1–1.9 $CH_2 \times 14$), 2.28 ($COCH_2$), 2.48 ($CH_2$), 3.16 ($CH_2$), 5.20 (CH).

Into a small volume of water, were dissolved the above white residue, 141 mg of N-[4-(3-aminopropyl)aminobutyl]-2,2-dihydroxyethanamide hydrochloride, and 42 mg of glutaric acid. The solution was heated at 60° C. for 24 hours. The reaction mixture was dissolved in aqueous methanol, passed through a column of Diaion® HP-20, which had been equilibrated with 0.5 M aqueous sodium chloride solution, and eluted with 90% aqueous methanol. The effluent was concentrated under reduced pressure to yield 23.9 mg of a white powder of 3-O-tetradecanoyl-GHA-GS trihydrochloride.

EXAMPLE 11. SYNTHESIS OF 3-O-BENZOYL-GHA-GS

Into 2.5 ml of dimethylformamide, was dissolved 2.09 of (S)-7-guanidino-3-hydroxyheptanamide hydrochloride followed by 1.7 ml of pyridine. To the solution, while being cooled in ice, was added slowly and dropwise 2.6 ml of benzoyl chloride. The mixture was stirred for 30 minutes while cooling in ice and for further two hours at room temperature. The reaction mixture was diluted with 20 ml of ice water, the separated oily layer was separated, and the aqueous layer was admixed with 600 mg of sodium chloride. The aqueous layer was passed through a column of Diaion® HP-20 which had been equilibrated with 0.5 M aqueous sodium chloride solution, and the column was washed successively with 0.5 M, 0.2 M and 0.1 M aqueous sodium chloride solutions, and with water. The fractions eluted with 20 to 40% (v/v) aqueous methanol were collected and concentrated under reduced pressure to yield 820 mg of (S)-7-guanidino-3-benzoyloxyheptanamide hydrochloride in oily form. NMR: 1.4–2.0 ($CH_2 \times 3$), 2.65 ($CH_2$), 3.17 ($CH_2$), 5.50 (CH), 7.2–8.1 ($COC_6H_5$).

Into 0.6 ml of water, were dissolved 384 mg of the above oily compound, 460 mg of N-[4-(3-aminopropyl)aminobutyl]-2,2-dihydroxyethanamide hydrochloride, and 148 mg of glutaric acid. The solution was heated at 50° C. for 2 days. The reaction mixture was diluted with water and passed through a column of CM-Sephadex® C-25 (Na-type). The fractions eluted with 0.52 to 0.56 M aqueous sodium chloride solutions were collected, concentrated under reduced pressure, passed through a column of Diaion® HP-20 equilibrated with 1 M aqueous sodium chloride solution, and washed with 0.1 M aqueous sodium chloride solution. The fractions eluted wth water and 30% aqueous methanol were collected, concentrated under reduced pressure, and further desalted by treating with a column of Sephadex® LH-20 to obtain 40 mg of a white powder of 3-O-benzoyl-GHA-GS trihydrochloride.

What is claimed is:

1. A composition selected from the group consisting of the epimeric mixture at position 2 of substances of Formula I, and the acid addition salts thereof Formula I

wherein R is hydrogen, alkanoyl of 1 to 14 carbon atoms, or benzoyl.

2. The compound of claim 1 wherein R is alkanoyl of 2 to 4 carbon atoms.

3. The hydrochloride salt of the substance of claim 1 or claim 2.

4. The compound of claim 1 wherein R is acetyl or the hydrochloride salt thereof.

5. The compound of claim 1 wherein R is propionyl or the hydrochloride salt thereof.

6. The compound of claim 1 wherein R is butyryl or the hydrochloride salt thereof.

7. The process for producing N-[4-(3-aminopropyl)aminobutyl]-2-[(S)-7-guanidino-3-hydroxyheptanamido]-2-hydroxyethanamide or a 3-O-acyl derivative thereof represented by the general formula (I)

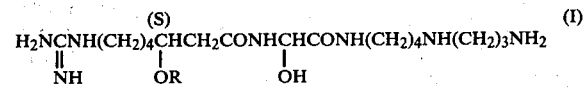

wherein R represents a hydrogen atom, an alkanoyl group of 1 to 14 carbon atoms, or an arylcarbonyl group, or an acid addition salt thereof, which comprises allowing a compound represented by the general formula (II)

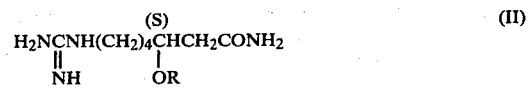

wherein R is as defined above or an acid addition salt thereof to condense with a compound represented by the formula (III)

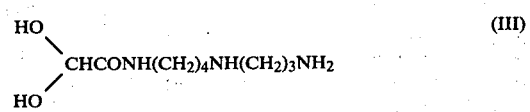

or an acid addition salt thereof in aqueous solution in the presence of an acid catalyst under application of heat.

8. The process according to claim 7, wherein R of the general formula II is an alkanoyl group of 2 to 4 carbon atoms.

9. The process according to claim 7, wherein the acid catalyst is a dicarboxylic acid.

10. The process according to claim 9, wherein the dicarboxylic acid is glutaric acid.

11. The process according to claim 7, wherein the amount of the acid catalyst is 0.5 to 10 moles per mole of the compound represented by the formula II.

12. The process according to claim 7, wherein the amount of water is 4 to 40 moles per mole of the compound represented by the formula II.

13. The process according to claim 7, wherein the reaction temperature is 30° to 70° C.

14. The process according to claim 7, wherein the reaction time is 1 to 2 days.

15. The method for inhibiting experimental murine leukemia which comprises systemically administering to a mammal bearing a tumor a non-toxic anti-tumor effective amount of a Compound of claim 2.

* * * * *

UNITED STATES PATENT AND TRADEMARK OFFICE
CERTIFICATE OF CORRECTION

PATENT NO. : 4,430,346

DATED : February 7, 1984

INVENTOR(S) : Hamao Umezawa et al.

It is certified that error appears in the above—identified patent and that said Letters Patent is hereby corrected as shown below:

On title page of patent [73] delete "Bristol-Myers Company, New York, N.Y." and in its place insert --- Zaidan Hojin Biseibutsu Kagaku Kenkyu Kai, Tokyo, Japan ---.

Signed and Sealed this

Ninth Day of July 1985

[SEAL]

Attest:

DONALD J. QUIGG

Attesting Officer     Acting Commissioner of Patents and Trademarks